United States Patent [19]

Arganbright

[11] Patent Number: 5,087,780
[45] Date of Patent: Feb. 11, 1992

[54] HYDROISOMERIZATION PROCESS

[75] Inventor: Robert P. Arganbright, Seabrook, Tex.

[73] Assignee: Chemical Research & Licensing Company, Houston, Tex.

[21] Appl. No.: 701,696

[22] Filed: May 14, 1991

Related U.S. Application Data

[63] Continuation of Ser. No. 264,355, Oct. 31, 1988, abandoned.

[51] Int. Cl.$^5$ ................................................ C07C 5/03
[52] U.S. Cl. ................................... 585/259; 585/670
[58] Field of Search ............................... 585/670, 259

[56] References Cited

U.S. PATENT DOCUMENTS

| | | | |
|---|---|---|---|
| 3,531,542 | 9/1970 | Myers et al. | 585/670 |
| 3,839,486 | 10/1974 | Arganbright | 585/670 |
| 4,215,011 | 7/1980 | Smith, Jr. | 252/426 |
| 4,232,177 | 11/1980 | Smith, Jr. | 585/324 |
| 4,242,530 | 12/1980 | Smith, Jr | 585/510 |
| 4,302,356 | 11/1981 | Smith et al. | 252/426 |
| 4,307,254 | 12/1981 | Smith et al. | 568/697 |
| 4,336,407 | 6/1982 | Smith, Jr. | 568/697 |
| 4,439,350 | 3/1984 | Jones, Jr. | 502/527 |
| 4,443,559 | 4/1984 | Smith et al. | 502/527 |
| 4,482,775 | 11/1984 | Smith, Jr. | 585/671 |
| 4,504,687 | 3/1985 | Jones, Jr. | 568/697 |
| 4,536,373 | 4/1985 | Jones, Jr. | 422/211 |
| 4,709,115 | 11/1987 | Jung et al. | 585/643 |

FOREIGN PATENT DOCUMENTS 1205677  9/1970  United Kingdom ............... 585/670

OTHER PUBLICATIONS

Boitiaux et al., "Newest Hydrogenation Catalysts", Hydrocarbon Processing, Mar. 1985, pp. 51–59.
Buseli, "Butene-1 to Polybutylene–Economic Outlook & Prospects", Abstract of Paper Presented to Division of Petroleum Chemistry, Inc. ACS., Mar. 1978.
Heck et al., "Catalytic Processes Using C$_4$ Streams for Octane Improvement: Hydro-Isomerization and MTBE", Paper Presented to Division of Petroleum Chemistry, Inc. ACS, Mar. 1980.

Primary Examiner—Asok Pal
Assistant Examiner—E. D. Irzinski
Attorney, Agent, or Firm—Kenneth H. Johnson

[57] ABSTRACT

A process for the isomerization of butenes in a mixed hydrocarbon stream containing butene-1, butene-2 and small amounts of butadiene in which the mixed hydrocarbon stream is fed to distillation column reactor containing an alumina supported palladium oxide catalyst as a distillation structure. As butene-1 is produced it is distilled off upsetting the equilibrium and allowing for a greater than equilibrium amount of butene-1 to be produced. Additionally, any butadiene in the feed is hydrogenated to butenes. The bottoms, which is rich in butene-2 may be recycled to the reactor column for more complete conversion of butene-2 to butene-1. Alternatively, a portion or essentially all of the bottoms, substantially free of butadiene, may be used for feed to an HF alkylation unit.

15 Claims, 1 Drawing Sheet

HYDROISOMERIZATION PROCESS

This application is a continuation of application Ser. No. 07/264,355, filed Oct. 31, 1988, now abandoned.

BACKGROUND OF THE INVENTION

There is a rapidly developing market for pure butene-1 for use as a monomer in the production of polybutylene. At the present time the commercial production of butene-1 requires isolation of a $C_4$ stream containing a relatively high concentration of the 1-isomer, for example, the product of steam cracking, followed by separation of butadiene by extractive distillation, extraction of isobutylene with dilute sulfuric acid and finally distillation. Other commercial methods include molecular sieve absorption of the linear olefins (efficiently used with low concentrations of n-butenes) and selective reaction of isobutylene to methyl-tertiary butyl ether (MTBE) followed by distillation of the unreacted olefins.

Isomerization of butene-2 to butene 1 has not normally been used because the equilibrium concentration of butene-1 in the mixture at reasonable temperatures is too low to allow economic separation by distillation. It has been known for some time that olefins can be isomerized under mild conditions using a catalyst of palladium oxide supported on alumina in the presence of hydrogen. The actual active catalyst is probably palladium hydride which is produced during operation. Sufficient hydrogen must be fed to maintain the catalyst in the active form because hydrogen is lost from the catalyst by hydrogenation or slow evolution from the hydride.

As commercialized, hydroisomerization is a process used to upgrade $C_4$ streams, usually from fluid catalytic cracking units. In the fixed bed process as practiced by some, butadiene contaminating the feed is hydrogenated to butenes, and the butenes are isomerized to the equilibrium mixture which is predominately butene-2. The advantage of that process is to remove butadiene which causes the loss of acid used in the alkylation process and improvement of the alkylate octane number in HF alkylation by using mostly butene-2 in the feed rather than butene-1.

Palladium catalysts are known and used for the butene-1 to butene-2 isomerization, As a matter of fact, because of its activity, one source, IFP, does not recommend palladium for use in streams where butene-1 is to be recovered.

According to the literature, isomerization occurs only after hydrogenation of the butadiene. In the fixed bed processes a three to four percent relative loss of butene occurs due to hydrogenation as the isomerization is pushed toward equilibrium.

The use of catalytic distillation processes is known in the art. See for example the series of patents assigned to Chemical Research and Licensing Company including U.S. Pat. Nos. 4,215,011; 4,232,177; 4,242,530; 8,302,356; 4,307,254; 4,336,407; 4,439,350; 4,443,559; 4,482,775; 4,504,687; 4,510,336; and 4,536,373. Catalytic distillation has been used in the isomerization of $C_4$ alkenes as noted in U.S. Pat. No. 4,482,775 listed above. However such a process used an acidic cationic exchange resin catalyst to produce iso and normal butenes.

The advantage sought to be achieved is relatively higher production levels of butene-1 which can be used as the monomer for polybutylene production. Another benefit would be to convert butadiene to butenes.

SUMMARY OF THE INVENTION

Briefly the present invention is a process for producing either butene-1 or butene-2 by the isomerization of normal $C_4$ olefins in the presence of a particulate supported PdO catalyst prepared as a distillation packing, preferably in the presence of a effectuating amount of hydrogen, and the concurrent distillation of the isomerization product to recover butene-1 as a light product or butene-2 as bottoms.

In light of the above a catalytic distillation process is provided which takes a mixed $C_4$ stream containing saturated $C_4$'s, butadiene and n-butenes and converts the butadiene to butenes and concentrates the two butene isomers in separate streams. Due to the "distillation" nature of the process butene-1 is produced overhead in greater concentration than equilibrium quantities. The feedstream, containing the mixed $C_4$'s is fed to the distillation reactor containing a supported palladium oxide catalyst along with sufficient hydrogen to provide for the hydrogenation of the butadiene. In the reactor the butadiene is converted to butenes and butene-1 is concentrated in the overhead.

Since the butene-1 is removed from the reaction zone, the isomerization is driven away from equilibrium and more butene-1 is produced than is obtained in an equilibrium reactor (fixed bed flow through). Saturated $C_4$'s are also concentrated by distillation in the overhead along with butene-1. Concentrated butene-2 may be removed from the distillation reactor as bottoms or is isomerized to butene-1 and taken overhead. The process may also be operated to produce substantially only a butene-2 bottoms stream by employing a 100% reflux of the butene-1 overhead.

DETAILED DESCRIPTION OF THE PREFERRED EMBODIMENTS

Figure 1:
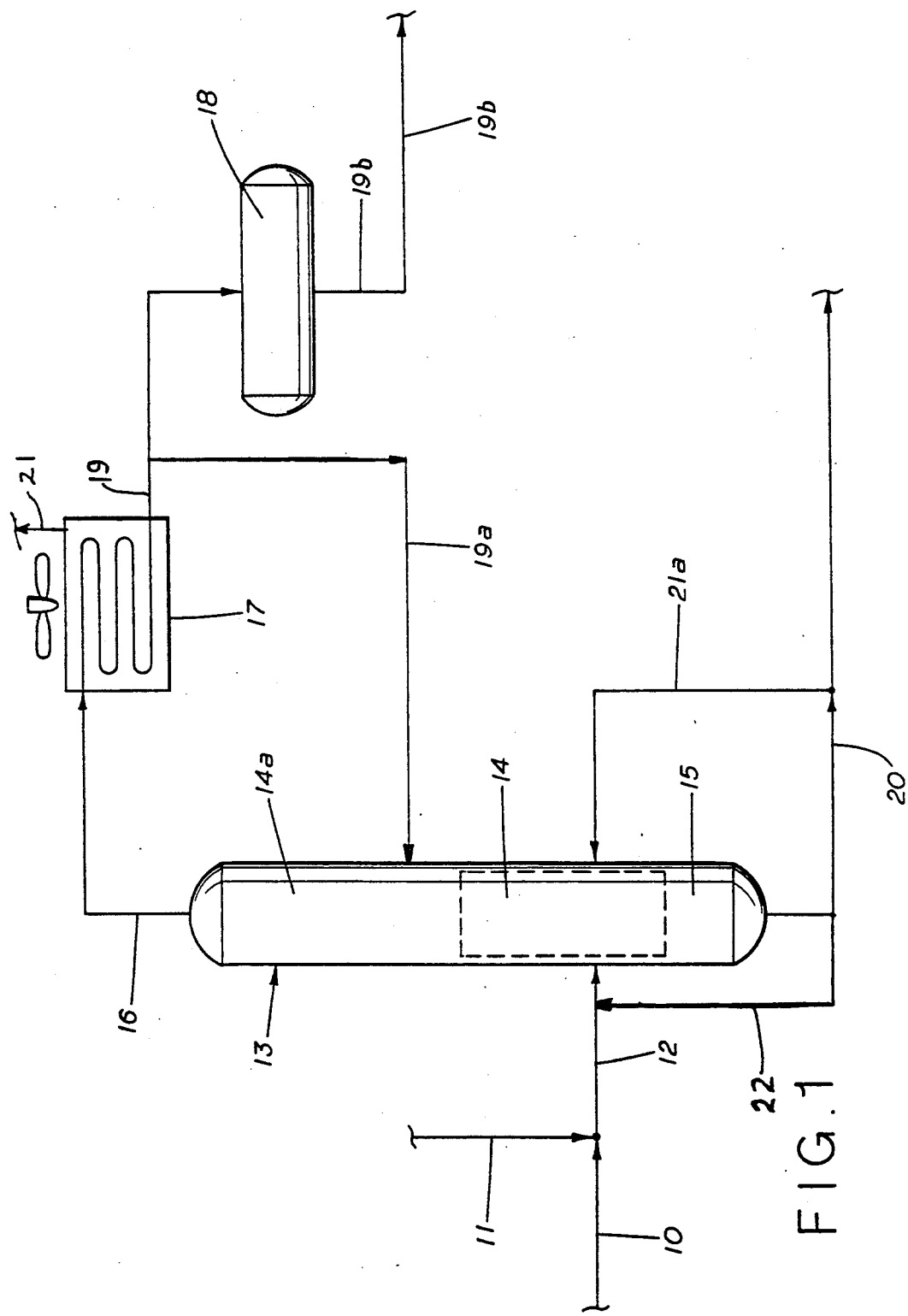
FIG. 1 is a schematic flow diagram of a preferred embodiment of the present invention.

The isomerization reaction is reversible as may be noted by references to "equilibrium" concentration in fixed bed reactors for a given residence time. In a catalytic distillation, i.e., the catalyst serves as a distillation component, the equilibrium is constantly disturbed, thus although the equilibrium concentration of butene-1 at a given temperature is rather low, the removal of butene-1 as an overhead product constantly drives the reaction to increase production of butene-1.

The catalytic material employed in the isomerization process must be in the form to serve as distillation packing; for example, rings, saddles, balls, irregular, sheets, tubes, spirals, packed in bags (as described in U.S. Pat. No. 4,242,530), plated on grills or screens, or reticulated polymer foams (the cellular structure of the foams must be sufficiently large so as not to cause high pressure drops through the column or otherwise arranged, such as in chunks or concentration tubes to allow vapor flow). Broadly stated, the catalytic material is a component of a distillation system functioning as both a catalyst and distillation packing, i.e., a packing for a distillation column having both a distillation function and a catalytic function.

The reaction system can be described as heterogenous since the catalyst remains a distinct entity. The catalyst may be employed in such conventional distillation packing shapes as Raschig rings, Pall rings, saddles or the like. Similarly the catalyst may be employed as palladium oxide supported on ⅛ alumina extrudates, either in bags or loosely packed in the column as described herein.

Experimentation has indicated that unpackaged (or unbagged) catalyst increases the pressure drop across the catalyst bed at high feed rates causing inefficient distillation which impedes the hydrogenation reaction. However it has been found that placing the supported catalyst into a plurality of pockets in a cloth belt, which is supported in the distillation column reactor by open mesh knitted stainless steel wire by twisting the two together into a helix, allows the requisite flows, prevents loss of catalyst, allows for normal swelling if any, of the catalyst and prevents breakage of the extrudates through mechanical attrition. This novel catalyst arrangement is described in detail in commonly owned U.S. Pat. Nos. 4,242,530 and 4,443,559 which are incorporated herein.

The cloth may be of any material which is not attacked by the hydrocarbon feeds or products or catalyst under the conditions of the reaction. Cotton or linen may be useful, but fiber glass cloth or TEFLON cloth is preferred. Briefly, a preferred catalyst system comprises a plurality of closed cloth pockets arranged and supported in the distillation column reactor by wire mesh intimately associated therewith.

The particulate catalyst material may be a powder, small irregular chunks or fragments, small beads and the like. The particular form of the catalytic material in the cloth pockets is not critical, so long as sufficient surface area is provided to allow a reasonable reaction rate. The sizing of catalyst particles can be best determined for each catalytic material (since the porosity or available internal surface area will vary for different material and of course affect the activity of the catalytic material).

The present invention carries out the method in a catalyst packed column which can be appreciated to contain a vapor phase and some liquid phase as in any distillation.

The success of the catalytic distillation approach lies in an understanding of the principles associated with distillation. First, because the reaction is occurring concurrently with distillation, the initial reaction products are removed from the reaction zone as quickly as possible. Second, because all the components are boiling the temperature of reaction is controlled by the boiling point of the mixture at the system pressure. The heat of reaction simply creates more boil up, but no increase in temperature. Third, the reaction has an increased driving force because the reaction products have been removed and cannot contribute to a reverse reaction (Le-Chatelier's Principle).

As a result, a great deal of control over the rate of reaction and distribution of products can be achieved by regulating the system pressure. Also, adjusting the throughput (residence time=liquid hourly space velocity$^{-1}$) gives further control of product distribution and degree of butene-2 to butene-1 conversion.

The temperature in the reactor is determined by the boiling point of the liquid mixture present at any given pressure. The temperature in the lower portions of the column will reflect the constitution of the material in that part of the column, which will be higher than the overhead; that is, at constant pressure a change in the temperature of the system indicates a change in the composition in the column. To change the temperature the pressure is changed. Temperature control in the reaction zone is thus effected by a change in pressure; by increasing the pressure, the temperature in the system is increased, and vice versa.

The reactor/distillation column is generally operated at overhead temperatures of 140° to 180° F. more preferably 140° to 160° F. at pressures in the range of 100 to 150 psig (bearing in mind the effect of pressure on temperature as discussed above.

A reflux is preferably included in the system. The reflux ratio could vary over the rate 0.5:1 to 33:1. In practice, the higher ratio may be used to compensate for a short catalyst bed such as required for experimental work. In commercial size units the catalyst bed would be provided so that lower reflux and hence higher unit productivity could be obtained at lower operating cost.

A catalyst suitable for the present process is 0.5% PdO on ⅛" $Al_2O_3$ (alumina) extrudates, hydroisomerization catalyst, supplied by Engelhard Industries. The catalyst is believed to be the hydride of palladium which is produced during operation. The hydrogen rate to the reactor must be sufficient to maintain the catalyst in the active form because hydrogen is lost from the catalyst by hydrogenation, especially when butadiene is contained in the feed. The hydrogen rate must be adjusted such that there is sufficient to support the butadiene hydrogenation reaction and replace hydrogen lost from the catalyst but kept below that required for hydrogenation of butenes and to prevent flooding of the column which is understood to be the "effectuating amount of hydrogen" as that term is used herein. Generally the mole ratio of hydrogen to $C_4$ hydrocarbon fed to the fixed bed of the present invention will be about 0.04 to 0.60, preferably 0.04 to 0.10.

The hydrocarbon stream is selected as one which is high in $C_4$'s, especially butene-2 for the butene-1 production or higher in butene-1 for butene-2 production. Saturated $C_4$'s only contribute to the vapor loading in the column. High concentrations of butadiene are not necessarily desired since it has been found that the isomerization reaction does not proceed until near completion of the butadiene hydrogenation reaction. A practical limit to butadiene is thus established by the reactor bed size and reaction time available for the hydrogenation and isomerization reactions. Additionally the butadiene can be extracted to practical limits before feeding due to its economic value. A typical candidate stream is the mixed $C_4$ stream from a fluid catalytic cracking unit (FCCU).

FIG. 1 is a schematic representation of a general process to selectively produce butene-1 while concentrating the butene-1 and butene-2 in separate streams. The initial step is combining a mixed $C_4$ stream 10, as from a butadiene extraction plant, with a hydrogen stream 11 and feeding the combined stream 12 to a distillation column reactor 13. The feed is introduced near the bottom of a catalytic distillation section 14 which is comprised of a plurality of the closed pocketed bags wrapped about demister wire in a helical shape with each of the pockets containing alumina supported PdO catalyst.

As the reactant feed contacts the catalyst any butadiene in the feed is hydrogenated to butenes and equilibrium amounts of butene-1 and butene-2 are produced at the catalyst. The butene-1 is immediately distilled off and taken overhead driving the reaction at the catalyst sites toward the production of butene-1.

Section 14a and 15 of the column are conventional distillation sections to allow for complete separation of the butene-1 and butene-2 products. Sufficient height of section 14a prevents butene-2 from being withdrawn overhead and internally "refluxes" it to the catalytic distillation section 14 where it is converted to butene-1.

Overhead stream 16, comprising butene-1 and the bulk of the saturated $C_4$'s is condensed in condenser 17. A portion of the overhead product 19 is recycled via 19a to the distillation column as reflux and the remainder is withdrawn and collected in receiver 18 as product 19b.

Bottoms 20 may be withdrawn or recycled via 22 to the catalytic distillation section 14 for complete conversion. The bottoms steam 20 rich in butene-2, but butadiene free, may also be used as feed to an HF alkylation unit where it has been shown to increase alkylate octane number.

The isomerization reaction proceeds at a rate of approximately 100 times faster than hydrogenation of the butenes, so the removal of the reactants from the reaction zones prevents loss of butenes. The hydrogen rate necessary for hydrogenation of butadiene is greater than that necessary for isomerization activity but less than that which would cause flooding in the tower. Unused hydrogen may be withdrawn from condenser 17 as gas stream 21 and recycled as necessary.

The following experimental examples were performed in a one inch diameter×6' laboratory unit which limited both the distillation reactor section and the normal distillation column. Consequently, complete separation of the butene-1 and butene-2 was not achieved. However the results clearly indicate that higher than equilibrium amounts of butene-1 is produced in the overheads and lower than equilibrium amount in the bottoms.

EXAMPLE I

The catalyst (47.0 grams of 0.5% PdO on ⅛" $Al_2O_3$ pellets from Engelhard) was placed in four bags and wrapped in distillation wire mesh packing. The bags were placed in the lower two foot section of a six foot by one inch distillation tower just above the bottoms section. Initial start up to obtain reflux at 100 psig was without hydrogen using a feed of butene-2 and n-butane (analysis shown in Table I). The reflux ratio was set at 100/4 initially (38 g. of raffinate in 18 min). Bottoms was withdrawn at approximately the same rate while feed was added to maintain bottoms level. The overhead was vented as required to maintain the pressure close to 100 psig (98 to 105 psig). The first 20 ml of distillate was discarded because of possible tower contamination. The initial bottoms sample was also discarded. Subsequently samples of about 38 g were taken in small steel bombs for analysis by GLPC (FID) via a liquid sampling valve. Material balance runs were made by taking weighed samples of both overhead and bottoms over the same time period.

The result of the experimental runs are shown in Table I and II.

Table III presents a comparison of overhead butene concentration with predicted equilibrium values at the same temperature. As can be readily seen, using the catalytic distillation process of the instant invention produced almost three to four times the equilibrium amount of butene-1 in the overhead.

Table IV shows the effect of loss of hydrogen feed. As may be seen the concentration of butene-1 in the overhead declined until hydrogen was reintroduced.

EXAMPLE II

Butadiene in Feed

Catalyst was loaded in the distillation column in a manner similar to Example 1. However the feed includes butadiene as shown in Table V. Only bottom samples were analyzed. Run II-57 indicates that isomerization does not occur so long a butadiene is present. Run II-60b shows that isomerization occurred using a feed containing butadiene when the hydrogen feed rate was sufficient to hydrogenate the butadiene. The isomerization rate was about the same as that obtained with no butadiene as in Run II-59a.

Run II-59b indicates the maximum isomerization possible using the laboratory column by analysis of the bottoms after fifty minutes on total reflux with continuous purge of hydrogen. The butene-1 to total butene ratio is only 2.7%. This may be compared to an expected equilibrium ratio at 155° F of 5.1%. This indicates that greater than expected amounts should b in the overhead.

Run II-61a and II-61b used chemically pure grade butene-1 as feed to determine the amount of olefin hydrogenation obtained during isomerization. The rate of isomerization as measured by the disappearance of butene-1 was about ten times as great as the rate using the earlier feed. The higher rate was probably due to the large difference between the concentration of butene-1 and the equilibrium concentration. However, the relative rate of isomerization as compared to hydrogenation is about 100 to 1. This suggests that about 1.0% of the normal olefin feed is lost by hydrogenation to butane. This is less than expected from a fixed bed reactor and can probably be decreased further by decreasing the feed of hydrogen to the minimum required for isomerization.

TABLE 1

Catalytic Distillation-Butene-2 Isomerization
Varied Hydrogen Feed and Reflux Rates

|  | Feed | OVER HEAD | OVER HEAD | OVER HEAD | OVER HEAD | OVER HEAD | OVER HEAD |
|---|---|---|---|---|---|---|---|
| Pressure, psig | — | 100 | 100 | 100 | 100 | 100 | 100 |
| Temp. F. (overhead) | — | 148 | 148 | 148 | 148 | 148 | 148 |
| $H_2$ Feed Rate, ml/min. | — | 0 | 54 | 300 | 300 | 300 | 20 |
| Reflux Ratio | — | 100/4 | 100/4 | 100/4 | 100/3 | 50/3 | 50/4 |
| Analyses, wt. % |  |  |  |  |  |  |  |
| n-butane | 32.01 | 39.95 | 40.71 | 38.37 | 37.37 | 34.26 | 30.41 |
| neopentane | 0.74 | 0 | 0 | 0 | 0 | 0 | 0 |
| butene-1 | 0.19 | 1.54 | 6.10 | 4.74 | 3.91 | 5.28 | 5.66 |
| Trans butene-2 | 41.84 | 42.11 | 41.80 | 43.87 | 44.66 | 46.54 | 46.91 |
| unknown | trace | 0 | 0.12 | 0 | 0.16 | 0 | 0 |
| cis butene-2 | 25.22 | 16.40 | 11.26 | 13.03 | 13.91 | 13.91 | 14.01 |

TABLE I-continued

Catalytic Distillation-Butene-2 Isomerization
Varied Hydrogen Feed and Reflux Rates

| | Feed | OVER HEAD | OVER HEAD | OVER HEAD | OVER HEAD | OVER HEAD | OVER HEAD |
|---|---|---|---|---|---|---|---|
| Prod. Rate g. $C_4$-1 per g. cat. hr. | — | 0.04 | 0.18 | 0.14 | 0.12. | 0.28 | 0.30 |

TABLE II

Catalytic Distillation-Butene-2 Isomerization
Material Balance Runs

| | RUN II-35 | | RUN II-33 | |
|---|---|---|---|---|
| | BTMS. | OVER HEAD | BTMS. | OVER HEAD |
| Pressure, psig | 100 | | 100 | |
| Temp. F. | 149 | | 145 | |
| $H_2$ Feed Rate, ml gas/min. | 54 | | 300 | |
| $C_4$ Feed Rate, ml liq/min. | 3.5 | | 3.5 | |
| Reflux Ratio | 100/2 | | 100/4 | |
| Analyses, wt. % | | | | |
| n-butane | 25.67 | 37.93 | 27.56 | 38.37 |
| neopentane | 1.23 | 0 | 1.50 | |
| butene-1 | 1.44 | 9.04 | 1.11 | 4.74 |
| unknown | 0.16 | 0.14 | | |
| trans-butene-2 | 47.29 | 42.94 | 43.68 | 43.87 |
| unknown | 0.7 | 0 | 0.19 | |
| cis butene-2 | 24.14 | 9.94 | 25.96 | 13.03 |
| sample wt. g. | 38 | 38 | 38 | 38 |
| Wt. % n-butane in total sample | 31.80 | | 32.96 | |
| wt. % n-butane in feed | 32.01 | | 32.01 | |

TABLE III

Catalytic Distillation - Butene-2 Isomerization
Comparison of Product Distribution With Equilibrium

| | OVER HEAD | OVER HEAD | EQUILIBRIUM |
|---|---|---|---|
| Pressure, psig | 100 | 100 | — |
| Temp. F. | 150 | 150 | 150 |
| $H_2$ Feed Rate, ml/min. | (a) | 20 | — |
| Reflux Ratio | 100/2 | 100/3 | — |
| Analyses,; Wt. % Excluding n-butane | | | |
| butene-1 | 17.75 | 13.09 | 4.90 |
| trans butene-2 | 68.06 | 69.26 | 72.0 |
| cis butene-2 | 14.19 | 17.65 | 23.1 |

(a) $H_2$ not fed during collection of sample (38 g.) but had been fed at 20 ml/min prior to that.

TABLE IV

Catalytic Distillation - Butene-1 Isomerization
Results after Hydrogen Feed Ceased

| | OVER HEAD | NEXT 38 g. OVER HEAD | NEXT 38 g. OVER HEAD | NEXT 50 g. OVER HEAD | OVER[a] HEAD |
|---|---|---|---|---|---|
| Pressure, psig | 100 | 100 | 100 | 100 | 100 |
| Temp. F. | 150 | 150 | 150 | 150 | 150 |
| $H_2$ Feed Rate, ml gas/min. | 54 | 0 | 0 | 0 | 54 |
| $C_4$ Feed Rate, ml liq/min. | 3.5 | 3.5 | 3.5 | 3.5 | 3.5 |
| Reflux Ratio | 100/4 | 100/4 | 100/4 | 100/4 | 100/4 |
| Analysis wt. % | | | | | |
| n-butane | 40.58 | 47.31 | 43.38 | 44.58 | 36.82 |
| butene-1 | 5.59 | 4.12 | 1.77 | 1.99 | 3.88 |
| trans butene-2 | 42.21 | 38.65 | 41.08 | 40.96 | 43.55 |
| Cis butene-2 | 11.46 | 9.77 | 13.77 | 12.31 | 15.58 |

[a] After hydrogen feed started again, second 38 g. overhead.

TABLE V

RESULTS OF HYDROISOMERIZATION OF BB FEED
WITH AND WITHOUT BUTADIENE-3[a]

| RUN NO. | II-57 | II-60b | II-59a | II-59b | II-61a | II-61b |
|---|---|---|---|---|---|---|
| Pressure psi | 150 | 150 | 155 | 155 | 152 | 152 |
| $H_2$ Feed rate ml/min. | 54 | 375 | 15–24 | 15–24 | 15–20 | 375 |
| Temp. F. | 170 | 180 | 180 | 180 | 177 | 177 |
| bottoms | | | | | | |
| cat. zone | 155 | 154 | 150–160 | 150–160 | 168/175 | 168/175 |
| overhead | 150 | 150 | 155 | 155 | 168 | 168 |
| Analysis, Feed wt. % | | | | | | |
| iso $C_4$ | 25.7 | 26.4 | 27.6 | 27.6 | 0.3 | 0.3 |
| $nC_4$ | 11.5 | 12.0 | 11.9 | 11.9 | 0.2 | 0.2 |
| $C_4$-1 | 11.5 | 11.9 | 12.9 | 12.9 | 99.0 | 99.0 |
| iso $C_4$— | 12.8 | 13.2 | 14.3 | 14.3 | 0.1 | 0.1 |
| trans $C_2$-2 | 17.9 | 18.7 | 20.4 | 20.4 | 0.3 | 0.3 |
| cis $C_4$-2 | 12.4 | 13.4 | 12.7 | 12.7 | 0.1 | 0.1 |
| butadiene | 2.7 | 0.6 | 0.0 | 0.0 | 0.0 | 0.0 |
| $C_5$3 s | 2.8 | 3.8 | — | — | — | — |
| Analysis, Bottoms wt. % | | | | | | |
| iso-$C_4$ | 11.1 | 6.5 | 17.2 | 7.7 | 0.1 | 0.0 |
| n-$C_4$ | 16.4 | 10.2 | 18.0 | 17.4 | 0.7 | 1.5 |
| $C_4$-1 | 11.5 | 2.6 | 4.7 | 1.6 | 35.5 | 10.5 |
| iso $C_4$- | 11.7 | 9.9 | 11.7 | 8.8 | trace | 0.0 |
| trans $C_4$-2 | 17.9 | 36.1 | 30.6 | 36.0 | 40.9 | 56.8 |
| cis $C_4$-2 | 12.4 | 21.9 | 17.3 | 22.7 | 22.8 | 31.2 |
| butadiene | 2.7 | 0.0 | 0.0 | 0.0 | — | — |
| $C_5$ | 2.8 | 4.8 | 0.4 | 5.8 | — | — |
| Isomerization Rate g. $C_4$-1/hr. g. cat. | 0.0 | 0.20 | 0.27 | total reflux | 1.76 | 2.22 |
| Hydrogenation Rate | — | — | — | — | 0.013 | 0.03 |

TABLE V-continued

RESULTS OF HYDROISOMERIZATION OF BB FEED
WITH AND WITHOUT BUTADIENE-3[a]

| RUN NO. | II-57 | II-60b | II-59a | II-59b | II-61a | II-61b |
|---|---|---|---|---|---|---|
| g. $C_4$/hr. g. cat. | | | | | | |

[a]Results from 1 inch tower.

The invention claimed is:

1. A process for the isomerization of $C_4$ alkenes comprising:
   (a) feeding a mixed $C_4$ stream at least partially in liquid phase and containing butene-1 and butene-2 to a distillation column reactor containing a fixed bed of alumina supported PdO catalyst prepared as a distillation structure,
   (b) concurrently feeding an effectuating amount of hydrogen to said fixed bed,
   (c) contacting said $C_4$ stream and said hydrogen with said fixed bed to isomerize said butene-2 to butene-1
   (d) withdrawing an overhead stream rich in said butene-1
   (e) withdrawing a bottom stream rich in said butene-2 and
   (f) returning a portion of said bottoms to said column to further convert butene-2 to butene-1.

2. The process of claim 1 wherein a portion of said overhead stream is returned to said column as reflux and the remaining portion withdrawn as overhead product.

3. The process of claim 1 wherein said mixed $C_4$ stream contains butadiene and said butadiene is hydrogenated to butene in said fixed bed.

4. The process of claim 2 wherein said reflux is returned to said column in a ratio of reflux to said overhead product of 0.5:1 to 33:1.

5. The process of claim 1 wherein said column is operated at about 100 to 150 psig and from 150° to 180° F.

6. The process of claim 1 wherein said hydrogen is fed to said fixed bed in a molar ratio to said $C_4$ stream of 4 about 0.04 to 0.60.

7. A process for the hydroisomerization of butene comprising
   (a) feeding a mixed hydrocarbon stream containing relatively high concentration of $C_4$'s especially n-butenes, and small amounts of butadiene and essentially no isobutylene to a distillation column reactor containing a fixed bed of alumina supported palladium oxide catalyst prepared as a distillation structure;
   (b) concurrently feeding an effectuating amount of hydrogen to said fixed bed;
   (c) concurrently in said distillation column
      (i) contacting said mixed hydrocarbon stream and said hydrogen stream to hydrogenate said butadiene to butenes and
      (ii) reacting a portion of said butenes to form butene-1,
   (d) withdrawing an overhead stream rich in said butene-1;
   (e) withdrawing a bottom stream rich in butene-2, said bottom stream being essentially free of butadiene; and
   (f) returning a portion of said bottoms stream to said column to further isomerize butene-2 to butene-1.

8. The process of claim 7 wherein said mixed hydrocarbon stream and said hydrogen stream are combined and subsequently fed to said distillation column reactor.

9. The process of claim 7 wherein a portion of said overhead stream is returned to said column as reflux.

10. The process of claim 7 wherein essentially all condensed liquid is removed from the bottom of the tower thereby maximizing isomerization to butene-2.

11. The process of claim 10 wherein the butene feed contains small amounts of butadiene and said butadiene is hydrogenated to butenes.

12. The process of claim 7 wherein essentially all condensed liquid is removed overhead from the tower thereby maximizing isomerization to butene -1.

13. In a process for isomerization of normal butene over an alumina supported palladium oxide catalyst in the presence of hydrogen, the improvement comprising placing said catalyst in a distillation column as a distillation structure such that butene-1 is removed overhead to continuously upset the equilibrium and thus produce greater than equilibrium amounts of butene-1.

14. The process of claim 7 wherein essentially all butene-2 is isomerized to butene-1 and removed overhead from the tower.

15. The process of claim 13 wherein butadiene is present and said butadiene is hydrogenated to butene.

* * * * *